United States Patent
Stanslaski et al.

(10) Patent No.: US 12,303,692 B2
(45) Date of Patent: May 20, 2025

(54) DEVICES AND METHODS FOR SENSING PHYSIOLOGICAL SIGNALS DURING STIMULATION THERAPY

(71) Applicant: MEDTRONIC, INC., Minneapolis, MN (US)

(72) Inventors: Scott Stanslaski, Shoreview, MN (US); Robert Devine, New Brighton, MN (US); Timothy Denison, Minneapolis, MN (US); Vincent Roczniak, Maple Grove, MN (US); Todd Smith, Shoreview, MN (US); Thomas Adamski, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 889 days.

(21) Appl. No.: 17/501,732

(22) Filed: Oct. 14, 2021

(65) Prior Publication Data
US 2022/0032065 A1     Feb. 3, 2022

Related U.S. Application Data

(60) Continuation of application No. 16/590,661, filed on Oct. 2, 2019, now Pat. No. 11,160,983, which is a
(Continued)

(51) Int. Cl.
*A61N 1/36*    (2006.01)
*A61N 1/05*    (2006.01)
*A61N 1/378*   (2006.01)

(52) U.S. Cl.
CPC ....... *A61N 1/36139* (2013.01); *A61N 1/0529* (2013.01); *A61N 1/0534* (2013.01);
(Continued)

(58) Field of Classification Search
CPC .............. A61N 1/36139; A61N 1/0529; A61N 1/0534; A61N 1/0553; A61N 1/3615; A61N 1/36178; A61N 1/378
See application file for complete search history.

(56) References Cited

U.S. PATENT DOCUMENTS 7,751,888 B1    7/2010   Schecter
9,238,141 B2    1/2016   Hocken et al.
(Continued)

FOREIGN PATENT DOCUMENTS

CN    105873635    8/2016
CN    106255526    12/2016
(Continued)

OTHER PUBLICATIONS

Chinese Application No. 201880014255.X Notice of Office Action, Feb. 22, 2023.
(Continued)

*Primary Examiner* — Lindsey G Wehrheim
(74) *Attorney, Agent, or Firm* — Shumaker & Sieffert, P.A.

(57) ABSTRACT

Devices and methods provide for the sensing of physiological signals by providing a stimulation waveform that includes a stimulation pulse followed by an active recharge pulse to clear the charge in capacitors within the stimulation path. The active recharge pulse is followed by a period of passive recharge and then a period of no recharge. Non-neurological sources of artifacts within the sensed physiological signal may be handled by providing a brief period of passive recharge followed by a lengthy period of no recharge, which is made possible by the use of the active recharge pulse prior to the passive recharge. The period of no recharge removes any low impedance path to ground from the stimulation electrodes, which allows an amplifier of the sensing circuit to provide common mode rejection of
(Continued)

non-neurological signals, such as cardiac signals, present at the sensing electrodes.

18 Claims, 10 Drawing Sheets

Related U.S. Application Data division of application No. 15/444,997, filed on Feb. 28, 2017, now Pat. No. 10,471,259.

(52) U.S. Cl.
CPC ......... *A61N 1/0553* (2013.01); *A61N 1/3615* (2013.01); *A61N 1/36178* (2013.01); *A61N 1/378* (2013.01)

(56) References Cited

U.S. PATENT DOCUMENTS

| | | | |
|---|---|---|---|
| 10,471,259 B2 | 11/2019 | Stanslaski et al. | |
| 11,160,983 B2 | 11/2021 | Stanslaski et al. | |
| 2003/0204223 A1 | 10/2003 | Leinders et al. | |
| 2006/0064149 A1 | 3/2006 | Belacazar et al. | |
| 2006/0224199 A1* | 10/2006 | Zeijlemaker | A61N 1/371 607/11 |
| 2010/0114209 A1 | 5/2010 | Krause et al. | |
| 2011/0295336 A1 | 12/2011 | Sharma et al. | |
| 2014/0163638 A1 | 6/2014 | Marnfeldt et al. | |
| 2014/0277268 A1 | 9/2014 | Lee | |
| 2015/0051670 A1 | 2/2015 | Hocken et al. | |
| 2015/0164354 A1 | 6/2015 | Parker et al. | |
| 2015/0223710 A1 | 8/2015 | Cong et al. | |
| 2015/0273217 A1 | 10/2015 | Legay et al. | |

FOREIGN PATENT DOCUMENTS

| | | |
|---|---|---|
| JP | 2014-522261 | 9/2014 |
| JP | 2016-503333 | 2/2016 |

OTHER PUBLICATIONS

International Preliminary Report on Patentability from International Application No. PCT/US2018/012758 dated Sep. 3, 2019, 7 pp.
Notice of Intent to Grant and Text Intended to Grant from counterpart European Application No. 18701867.6 dated Feb. 12, 2021, 70 pp.
Notice of Intent to Grant and Text Intended to Grant from counterpart European Application No. 18701867.6 dated Oct. 20, 2021, 144 pp.
Notice of Intent to Grant, and translation thereof, from counterpart Japanese Application No. 2019-544646 dated Jul. 26, 2022, 5 pp.
Prosecution History from U.S. Appl. No. 15/444,997, now issued U.S. Pat. No. 10,471,259, dated Oct. 3, 2018 through Jul. 2, 2019, 31 pp.
Prosecution History from U.S. Appl. No. 16/590,661, now issued U.S. Pat. No. 11,160,983, dated Mar. 31, 2021 through Aug. 18, 2021, 24 pp.
Response to Communication Pursuant to Rules 161(1) and 162 EPC dated Oct. 7, 2019, from counterpart European Application No. 18701867.6, filed Mar. 12, 2020, 14 pp.
Japanese Patent Application No. 2019-544646, Office Action, Jun. 15, 2021.
PCT Application No. PCT/US2018/012758 International Search Report and Written Opinion, May 8, 2018.
Japanese Patent Application No. 2019-544646, Office Action, Jan. 24, 2022.

* cited by examiner

FIG. 14

DEVICES AND METHODS FOR SENSING PHYSIOLOGICAL SIGNALS DURING STIMULATION THERAPY

RELATED APPLICATIONS

This application is a continuation of U.S. Pat. No. 11,160,983, which is a divisional of U.S. Pat. No. 10,471,259.

TECHNICAL FIELD

Embodiments provide devices and methods for sensing physiological signals. More particularly, embodiments provide devices and methods for sensing physiological signals while stimulation therapy is being conducted.

BACKGROUND

Electrical stimulation therapy may be used for various forms of treatment. For example, stimulation therapy may be provided to address neurological issues such as chronic pain, tremors, and the like. In such an example, an implantable stimulation device is typically located in one location of convenience and is connected to electrical leads that are routed to a stimulation site such as within the brain, within the spinal column, within the pelvic region, or elsewhere. The electrical leads include electrodes that interface with the tissue at the stimulation site to deliver the stimulation signals from the stimulation device.

It may be useful to also sense physiological signals nearby the stimulation site. Such signals may be useful to tailor the stimulation therapy to the particular condition being treated and/or to better understand the response of the tissue nearby the stimulation site to the stimulation signals. Sensing physiological signals may be especially useful where the stimulation therapy may be at least partially controlled based on the physiological signals.

Sensing physiological signals in proximity to the stimulation site can be problematic particularly for neurological stimulation systems. Other signals that may be present within the body nearby the stimulation site may have a voltage that is orders of magnitude greater than the neurological signal to be sensed. For instance, electrical signals produced by the cardiac system can be very problematic considering the heart may be located in close proximity to the neurostimulation device and leads, especially in the case of deep brain stimulation therapy when the device is located in the upper torso.

SUMMARY

Embodiments address issues such as these and others by providing devices and methods that reduce the likelihood of non-neurological signals producing unwanted artifacts in the sensed physiological signals. Some embodiments provide for active recharge to occur after the stimulation pulse and then passive recharge to occur briefly after the active recharge. The recharge is then turned off for the remainder of the period occurring before the next stimulation pulse which provides an adequate amount of time to sense the physiological signals of interest, such as neurological signals. While the recharge is off, there is no low impedance path to the device ground potential which prevents any significant amount of cardiac or other non-neurological produced current from flowing through signal pathways leading to differential inputs of the sensing amplifier. As a result, the non-neurological signal presents essentially the same voltage across both differential inputs of the sensing amplifier such that common mode rejection of the non-neurological signal occurs.

Embodiments provide a method of providing stimulation and sensing physiological signals that involves providing a first stimulation pulse from a first electrode within a body and after the first stimulation pulse terminates, providing an active recharge pulse from the first electrode. The method further involves after a termination of the active recharge pulse, providing a passive recharge from the first electrode and after a termination of the passive recharge, providing no recharge for a period of time. The method also involves during at least a portion of the period of time of no recharge, sensing physiological signals from a second electrode within the body and after the period of time of no recharge, providing a second stimulation pulse from the first electrode.

Embodiments provide an implantable medical device that includes a stimulation output and a stimulation engine that provides a waveform to the stimulation output, the waveform including a stimulation pulse followed by an active recharge pulse followed by a passive recharge followed by a period of time of no recharge. The implantable medical device further includes a first sensing input and a differential amplifier connected to the first sensing input. The implantable medical device also includes a controller that obtains physiological signals from the differential amplifier during at least a portion of the period of time of no recharge, the controller causing the stimulation engine to produce the waveform repeatedly.

Embodiments provide an implantable medical system that includes at least one implantable medical lead comprising a first electrode and a second electrode. The implantable medical system further includes an implantable medical device that has a stimulation output electrically coupled to the first electrode. The implantable medical system also includes a stimulation engine that provides a waveform to the stimulation output. The waveform includes a stimulation pulse followed by an active recharge pulse followed by a passive recharge followed by a period of time of no recharge. The implantable medical system also includes a first sensing input electrically coupled to the second electrode and a differential amplifier connected to the first sensing input. The implantable medical system includes a controller that obtains physiological signals from the differential amplifier during at least a portion of the period of time of no recharge, and the controller causes the stimulation to produce the waveform repeatedly.

DETAILED DESCRIPTION

Embodiments provide medical devices and related methods that minimize the presence of non-neurological signal artifacts on a sensed signal. Embodiments utilize a stimulation waveform that includes an active recharge period followed by a passive recharge period and then a period of no recharge where sensing is performed at least during the period of no recharge. Some embodiments determine whether there are non-neurological signal artifacts present in the sensed signal while using passive recharge without active recharge and then switch to using active recharge followed by passive recharge when non-neurological signal artifacts are present. Furthermore, some embodiments optimize the ratio of active recharge amplitude to stimulation pulse amplitude to further minimize the artifacts.

Figure 1:
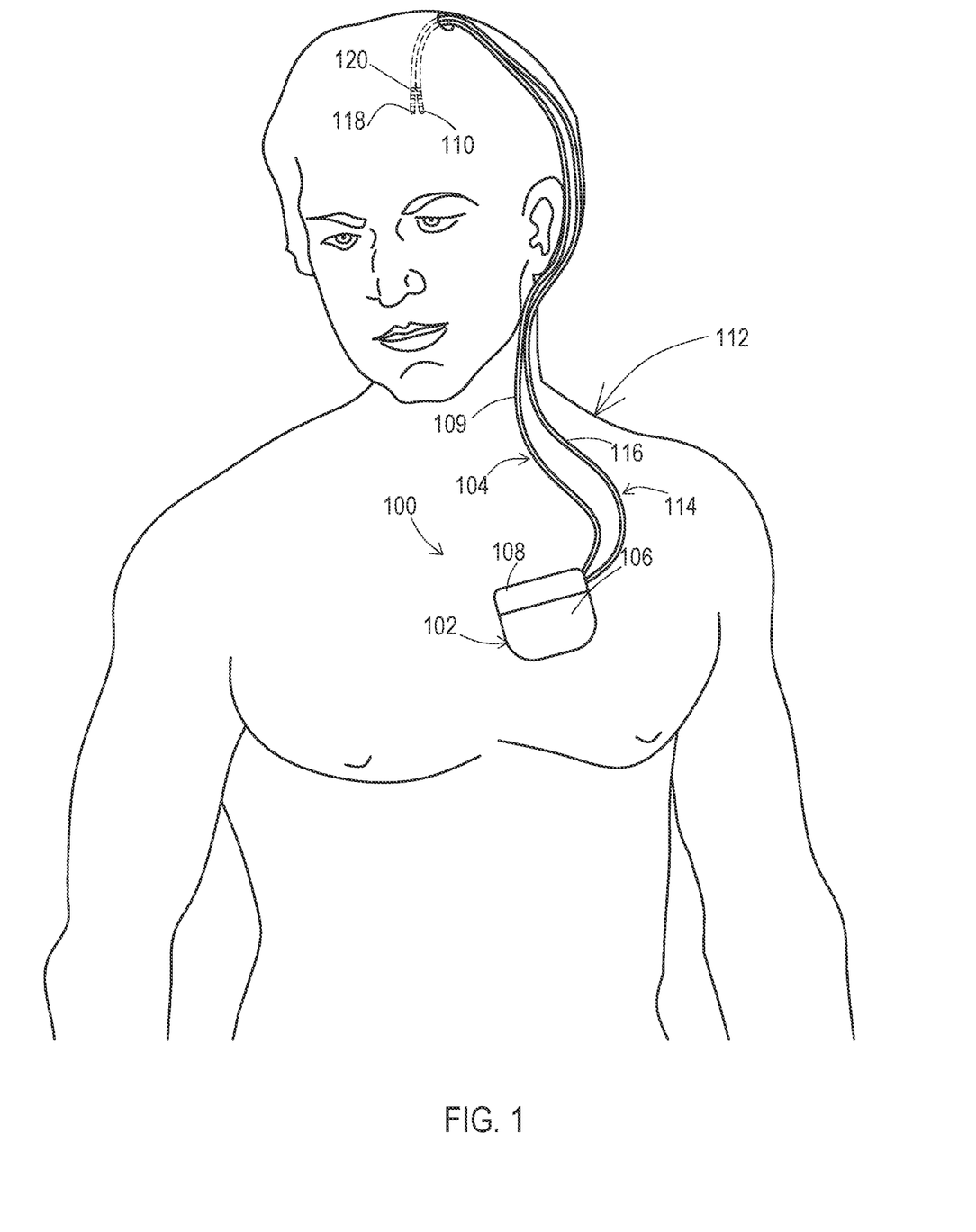
FIG. 1 shows a patient having an example of an implantable medical system for sensing physiological signals concurrently with providing stimulation signals according to various embodiments.

FIG. 1 shows an example of an operating environment for the various embodiments. An implantable medical system 100 is implanted within a body of a patient 112. The implantable medical system 100 includes a stimulation and sensing device 102 coupled to a stimulation lead 104. The stimulation and sensing device 102 includes a conductive outer casing 106 as well as a header 108 that includes a bore where a proximal end of the stimulation lead 104 is positioned. The stimulation lead 104 includes a lead body 109 and one or more electrodes 110 on a distal end of the lead body 109 which is positioned at a stimulation site within the body of the patient 112. The stimulation device 102 produces stimulation signals that are delivered through conductors of the stimulation lead 104 to the electrodes 110 where those stimulation signals enter the tissue of the patient 112.

In this example, the header 108 also includes a bore where a proximal end of a sensing lead 114 is positioned. The sensing lead 114 includes a lead body 116 and one or more electrodes 118, 120 that are positioned in proximity to the stimulation site within the body of the patient 112 so as to be able to capture physiological signals emanating from the stimulation site. The stimulation and sensing device 102 provides a mode of capacitor recharge and senses the physiological signals when non-neurological signals may be present within the patient 112.

The foregoing example provides stimulation lead 104 dedicated to providing the stimulation signal and sensing lead 114 dedicated to sensing the physiological signal. In still another example, the same one or more leads may be used to provide both the stimulation and sensing function. For instance, one or more electrodes of a single lead may be used to deliver stimulation signals to the tissue of patient 112 and one or more different electrodes of that same lead may be used to sense physiological signals emanating from the stimulation site. Alternatively, multiple electrodes residing on multiple leads may be used to deliver the stimulation signals while one or more electrodes provided by one or both of the multiple leads may be used to sense the physiological signals. In such cases, the lead is electrically connected to both the stimulation engine and the sensing circuit, this option being shown as dashed lines in FIG. 2 discussed below. In some examples, a same electrode used to provide stimulation signals may be used to perform sensing. In such examples, one or more switches may be used to selectively connect the stimulation engine 206 and sensing circuit 204 to the same electrode. For instance, the stimulation engine 206 may be disconnected from the electrode prior to connecting the sensing circuit 204 to the electrode, and so on. In such a case, the switch of the electrode to sensing mode begins once recharge has completed such that the electrode is no longer involved in providing the recharge path.

The one or more leads used for providing the stimulation signals and for sensing the physiological signals may be of various types. In one example, a lead having a simple electrode array geometry may be used for stimulation and/or for sensing. An example of a simple electrode array geometry may include one or more ring electrodes distributed at different axial positions along the length of a lead. Another example of a simple electrode array geometry is a planar array of electrodes on a paddle lead such as for spinal stimulation sites.

In another embodiment, one or more leads used for providing the stimulation signal and for sensing the physiological signals may have a complex electrode array geometry. A complex electrode array geometry generally refers to an arrangement of stimulation electrodes at multiple non-planar or non-coaxial positions, in contrast to simple electrode array geometries in which the electrodes share a common plane or a common axis. An example of a complex electrode array geometry, in accordance with this disclosure, is an array of electrodes positioned at different axial positions along the length of a lead, as well as at different angular positions about the periphery, e.g., circumference, of the lead. In some embodiments, the electrodes in the complex array geometry may appear similar to non-contiguous, arc-like segments of a conventional ring electrode. A lead with a complex electrode array geometry may include multiple "rings" of such electrode segments. Each ring is disposed at a different axial position. Each electrode segment within a given ring is disposed at a different angular position. The lead may be cylindrical or have a circular cross-section of varying diameter. Such a lead may be referred to as a "segmented" lead.

Another example of a complex electrode array geometry is an array of electrodes positioned on multiple planes or faces of a lead. As an illustration, arrays of electrodes may be positioned on opposite planes of a paddle lead or multiple faces of a lead having a polygonal cross-section, particularly for spinal stimulation sites. Examples of complex array geometries are shown and described in U.S. Pat. No. 7,822,483 entitled "Electrical and Activation Field Models for Configuring Stimulation Therapy" which is assigned to the assignee of the present application and which is incorporated herein by reference. Other types of sensing and/or stimulation electrodes may be used according to the current disclosure, including conformable electrodes, cuff electrodes, segmented electrodes, or any other type of electrodes capable of forming unipolar, bipolar or multi-polar electrode configurations.

The stimulation signals may be delivered using various electrode arrangements such as unipolar arrangements, bipolar arrangements or multipolar arrangements. A unipolar stimulation arrangement generally refers to the use of an anode on the conductive outer casing 106 that sources current and one or more cathodes on one or more leads (e.g., 104, 114) that sink current. A bipolar stimulation arrangement generally refers to the use of an anode on a lead (e.g., lead 104) that sources current and a cathode on the same lead and/or another lead that sinks current. A multipolar stimulation arrangement generally refers to the use of more than one anode on a lead (e.g., lead 104) that each source current and one or more cathodes on the same lead or another lead that sink current, or the use of one anode on a lead that sources current and multiple cathodes on the same lead or another lead that sink current.

A hybrid stimulation arrangement that combines both unipolar and bipolar electrode relationships may be referred to as an omnipolar arrangement. In an omnipolar arrangement, an anode on the housing may be used to deliver stimulation pulses substantially simultaneously with at least one anode on a lead and at least one cathode on a lead. In this case, for an omnipolar arrangement, at least one anode on a lead and at least one anode on the housing can be used simultaneously in combination with at least one cathode on a lead. In other omnipolar arrangements, a cathode on the housing may be used to deliver stimulation pulses substantially simultaneously with at least one cathode on a lead and at least one anode on a lead. In this alternative case, for an omnipolar arrangement, at least one cathode on a lead and at least one cathode on the housing can be used simultaneously in combination with at least one anode on a lead. Any of the above electrode arrangements, or other electrode arrangements, may be used to deliver electrical stimulation in accordance with techniques described in this disclosure.

Figure 2:
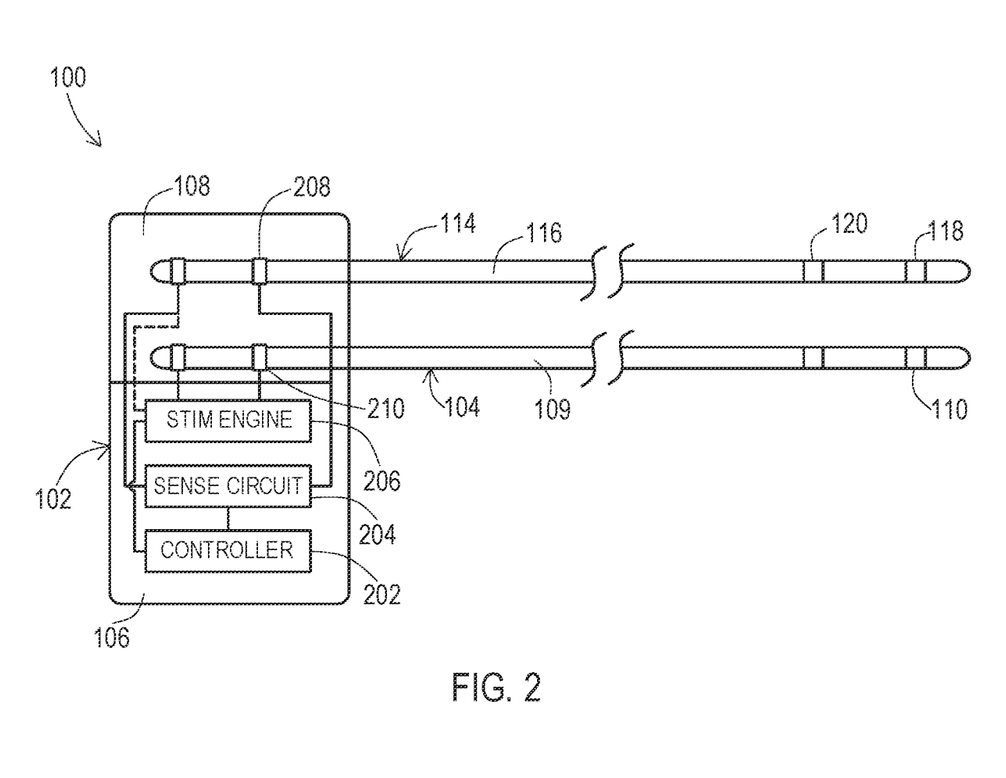
FIG. 2 shows an implantable medical system including a medical device attached to a stimulation lead and a sensing lead or to a sensing and stimulation lead.

FIG. 2 shows the implantable medical system 100 in more detail. Here, the stimulation device 102 includes a stimulation engine 206, a sensing circuit 204, and a controller 202. A conventional stimulation engine 206 produces the stimulation pulses and recharge pulses applied to the stimulation pathway via electrical connections 210 to the stimulation lead 104 within the header block 108. The sensing circuit 204 captures the physiological signals via connections 208 to the sensing lead 114 within the header block 108. In an embodiment where the sensing and stimulation function are provided by one or more of the same leads, both the stimulation engine 206 and sense circuit 204 may be coupled to the same one or more leads, as appropriate. Such an option is illustrated for the lead 114 of FIG. 2 with a dashed line indicating the optional electrical connection of the stimulation engine 206 being electrically connected to the lead 114 where one of the electrodes 118 or 120 is being used for stimulation while the other electrode is being used for sensing.

Stimulation engine 206 may provide voltage-controlled stimulation or current-controlled stimulation during various forms of therapy. A specific example of electrical stimulation parameters and corresponding ranges for the stimulation engine 206 to implement that are believed to be effective in deep brain stimulation (DBS) therapy to manage a movement disorder of a patient includes:

1. Frequency: the stimulation signal can include signal components within a first range of frequencies, for example, between approximately 0 Hz and approximately 10,000 Hz, or in some examples between approximately 0 Hz and approximately 500 Hz, or between approximately 2 Hz and approximately 250 Hz.
2. Voltage Amplitude: between approximately 0 volts and approximately 50 volts, such as between approximately 0 volts and approximately 25 volts.
3. Current Amplitude: A current amplitude may be between approximately 0 milliAmps and approximately 40 milliAmps, or approximately 0 to 25 milliAmps.
4. Pulse Width: between approximately 1 microseconds and approximately 5000 microseconds, such as between approximately 10 microseconds and approximately 1000 microseconds, or between approximately 10 microseconds and approximately 450 microseconds.

The sensing circuit 204 may capture the physiological signals in proximity to the stimulation site by avoiding the stimulation signal. For instance, the sensing circuit 204 may utilize blanking during the stimulation signal as well as during the active recharge portion, if any, after the stimulation signal. The stimulation pulse and active recharge pulse therefore do not negatively impact the sensing circuit 204 such that the sensing circuit 204 can capture accurate physiological data during the time between the stimulation pulses.

In this example, the controller 202 orchestrates the operation of the sensing circuit 204 and the stimulation engine 206. The controller 202 activates and deactivates various phases of operation of the stimulation that occur during stimulation therapy. The phases may include a stimulation output phase where the stimulation pulse is delivered, and a recharge phase that clears voltage on coupling capacitors in the stimulation path within the stimulation engine 206. The phases may also include a period of no recharge. Likewise, the controller 202 activates blanking switches of the sensing circuit 204 to blank the stimulation signal and at least a portion of a passive recharge signal such as the peak of the passive recharge signal when a passive recharge signal is used alone. For an active recharge pulse followed by a brief passive recharge signal followed by a lengthy period of no recharge, some of the passive recharge signal may be blanked in addition to blanking some or all of the active recharge pulse, depending upon the desired amount of time to sense the physiological signal.

The controller 202 may be of various forms. For instance, the controller 202 may comprise a general purpose programmable processor that implements programming instructions to bring about the operation of the stimulation engine 206 and the sensing circuit 204. As other examples, the controller 202 may comprise a dedicated purpose processor and/or hardwired digital logic.

Figure 3:
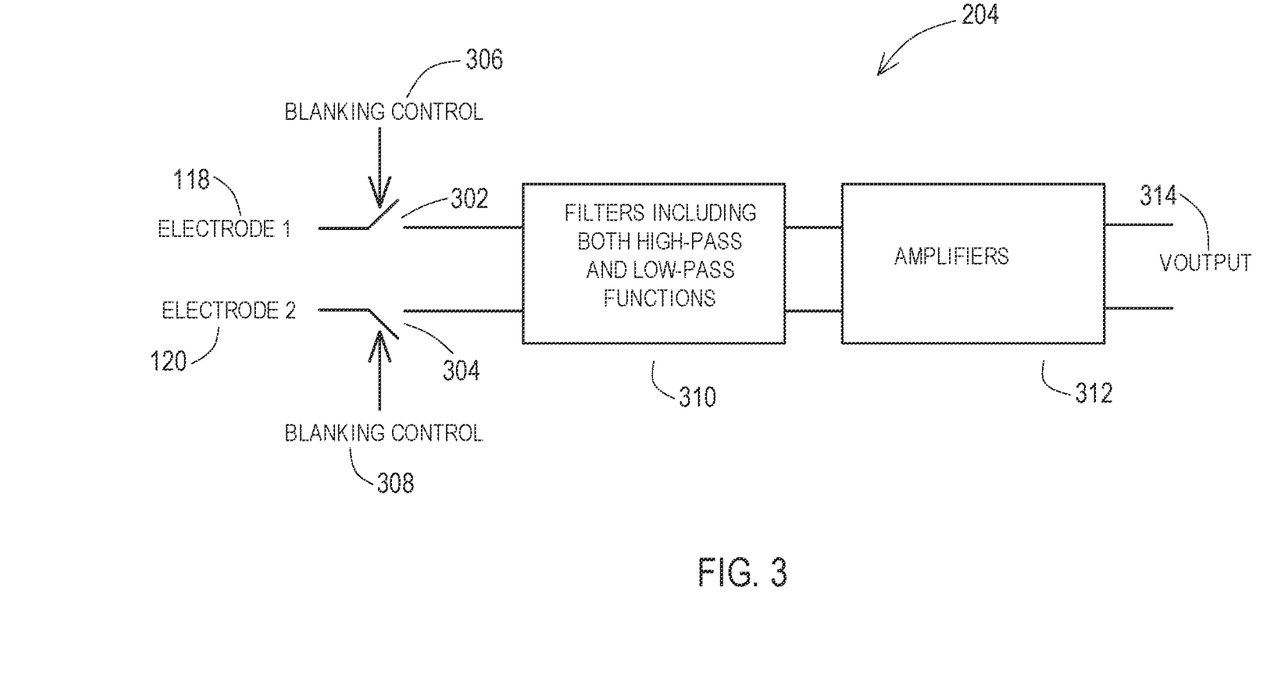
FIG. 3 shows an example of sensing circuitry of a medical device that implements active recharge, passive recharge, and a large period of no recharge.

FIG. 3 shows an example of the sensing circuit 204 that blanks the stimulation pulse as well as some or all of the active recharge pulse, if any. Each sensing electrode 118, 120 is electrically coupled to a blanking switch 302, 304 that is controlled by the controller 202. The blanking switches may be implemented in silicon such as individual transistors or in more complex arrangements as discussed below. The controller 202 provides a blanking control signal 306, 308 that causes the switches to either conduct signals or stop conducting the signals from the electrodes 118, 120. The switches 302, 304 conduct from a time after the recharge phase to a time before the beginning of the next stimulation phase and stop conducting at least during the stimulation phase and the peak of the following recharge phase in order to blank the stimulation artifacts from the sensed signal.

The blanking switches 302, 304 may be followed in the respective signal path by filters 310 that include both high pass and low pass filters that remove extraneous frequencies from the sensed signal. The filtered signals are provided as input to conventional differential amplifiers 312 that scale the amplitude as desired to produce the sensed signal output 314. The filters 310 may include a high pass filter to decouple from DC which can occur during the blanking period. The filters 310 may include a low pass filter to avoid waveform spread and to avoid a rectification effect from high frequency interferences.

Figure 4:
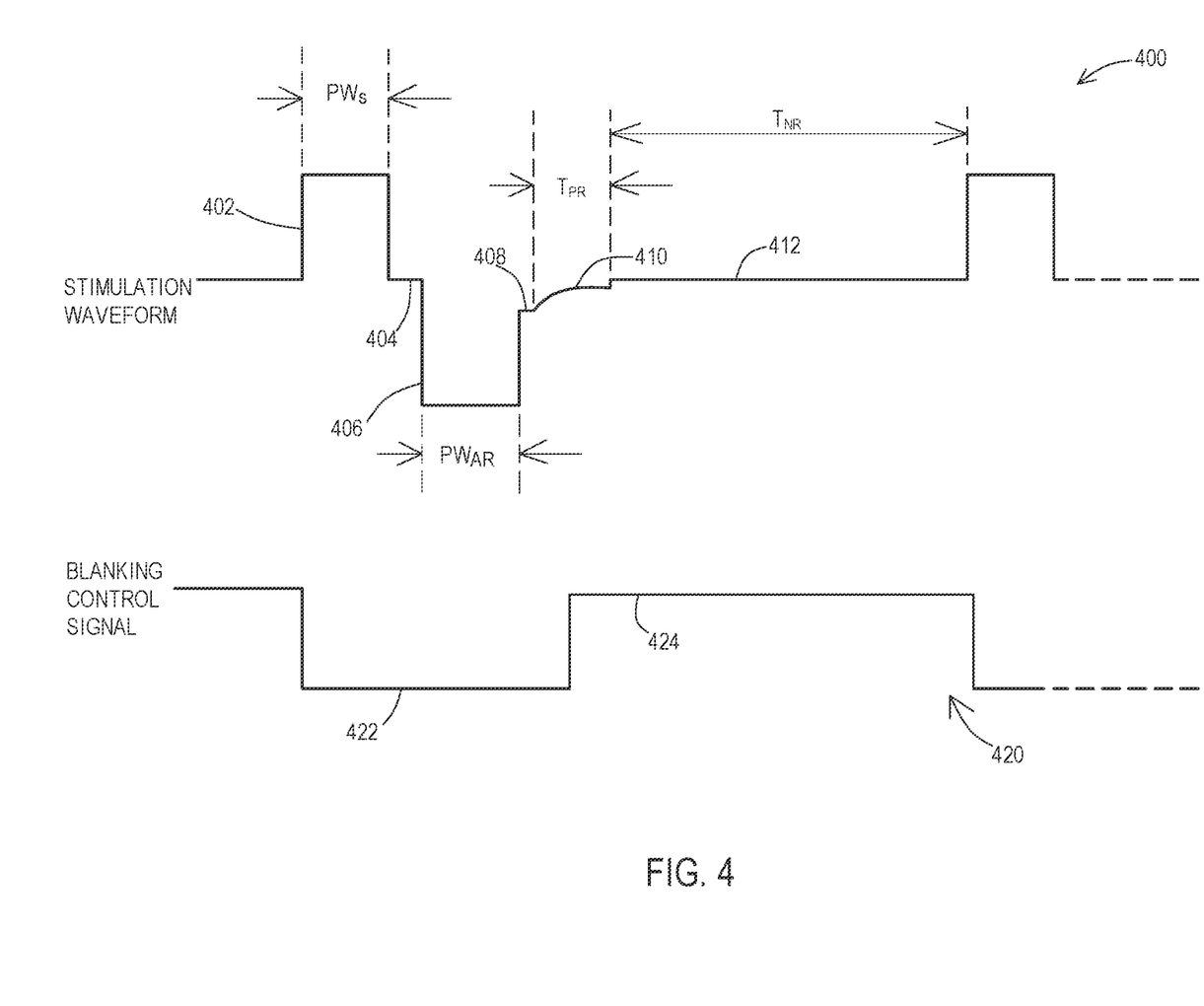
FIG. 4 shows a first example of a stimulation waveform including active recharge, passive recharge, and a large period of no recharge and with a corresponding sensing state.

FIG. 4 shows a set of signals and their related timing including a stimulation therapy waveform 400 and a blanking control signal 420. As can be seen, the stimulation therapy waveform 400 includes a stimulation pulse 402 having a pulse width PWs, followed by a relatively brief off period 404 (e.g., 64-96 μs) then followed by an active recharge pulse 406 of opposite polarity. By using active recharge, the recharge pulse 406 may be provided with a steady amplitude rather than decaying like a passive recharge pulse. The active recharge pulse 406 may also have a larger amplitude than the peak of a passive recharge pulse, thus the amount of time to provide the recharge to clear the capacitors is drastically reduced. Furthermore, it is beneficial to the elimination of the artifacts from a non-neurological signal to clear the capacitors prior to sensing the physiological signal. Therefore, as in this example, the active recharge pulse 406 is provided very soon after the end of the stimulation pulse 402.

The blanking control signal 420 is held at an amplitude that biases the blanking control switches to the conducting state to allow current flow. However, the blanking control signal 420 includes an inverted pulse 422 that unbiases the blanking control switches from the conducting state to the non-conducting state to prohibit current flow. The blanking control signal 420 is synchronized in time to the stimulation waveform 400 such that the blanking control signal inverted pulse 422 begins just before the stimulation pulse 402 and terminates just after the recharge pulse 406. The blanking control signal inverted pulse 422 thereby causes current flow to be blocked during the entire stimulation pulse 402 and at least a large portion of the active recharge pulse 406.

The active recharge pulse 406 has a pulse width $PW_{AR}$ that may be pegged to the pulse width of the stimulation pulse 402. The amplitude of the active recharge pulse 406 may then be set to effectively clear the capacitors in the amount of time of the pulse width. As noted above, clearing the capacitors assists in eliminating the signal artifacts. One manner of ensuring this to be the case is to set the active recharge amplitude to some ratio of the stimulation pulse amplitude, measure the sensed signal, adjust the ratio, and repeat until the signal artifacts are minimized. This is discussed in more detail below with reference to FIG. 9.

Once the active recharge pulse 406 has completed, and after a very brief period 408 (e.g., 8-12 μs) of no recharge 408 has occurred while passive recharge switches of the stimulation engine transition to a conductive state, a period of passive recharge 410 occurs. The passive recharge 410 finishes the balancing of the capacitors to fully prepare the capacitors for the next stimulation pulse which avoids loss of stimulation amplitude and avoids any charge neutrality issues. The duration of the passive recharge 410, $T_{PR}$, may be set to a particular fixed value (e.g., 264-396 μs) and then allow the active recharge ratio to be adjusted, in light of that fixed duration of passive recharge, to effectively clear the capacitors and minimize signal artifacts.

A relatively lengthy period of no recharge 412 then follows the period of passive recharge 410. The period of no recharge 412 has a duration $T_{NR}$ that is equal to the amount of time available between the end of the passive recharge 412 and the beginning of the next stimulation pulse. This next stimulation pulse occurs in accordance with the given rate of stimulation currently being used by the stimulation engine.

At some point near the end of the active recharge pulse 406 and the beginning of the period of no recharge 412, the blanking switches are reversed as indicated by the reversal of the state of the blanking signal 420 at signal portion 424. During signal portion 424, the blanking switches conduct the received signal to allow for capturing and amplifying the sensed signal. Thus, the sensed signal is being captured and amplified at least during the period of no recharge 412. In some embodiments, the sensed signal may also be captured and during some or all of the passive recharge 410 and potentially during an ending portion of the active recharge pulse 406 or off period 408.

Figure 5:
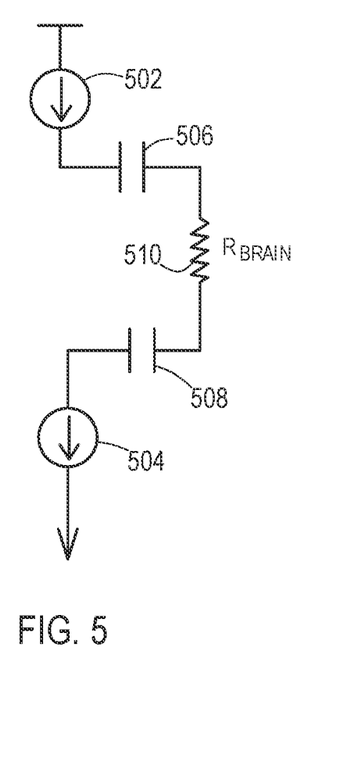
FIG. 5 shows a first stimulation engine circuit configuration used for providing the stimulation pulse portion of the stimulation waveform.

FIGS. 5-8 illustrate examples of circuit configurations that the stimulation engine may utilize to bring about each of the phases of the stimulation waveform 400 of FIG. 4. FIG. 5 specifically shows the configuration for producing the stimulation pulse 402. The stimulation engine of this example includes a first current source 502 that forces current through a first capacitor 506 of the stimulation path, through the tissue of the body where the stimulation electrodes are located (e.g., the resistance provided by the brain, $R_{BRAIN}$), and through another capacitor 508 of the stimulation path. A second current source 504 pulls this current to system ground. While multiple current sources a 502, 504 are shown, it will be appreciated that a single current source may be used instead. Additionally, while current sources are shown in FIG. 5, it will be further appreciated that one or more voltage sources may be used instead.

Figure 6:
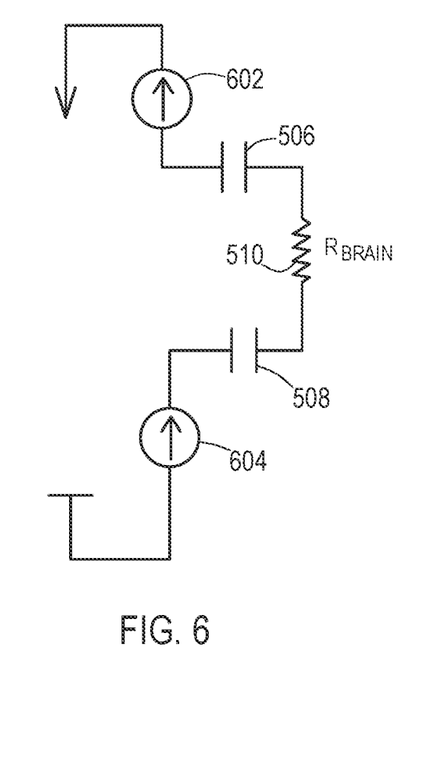
FIG. 6 shows a second stimulation engine circuit configuration used for providing the active recharge pulse portion of the stimulation waveform.

FIG. 6 specifically shows the configuration for producing the active recharge pulse 406. The stimulation engine of this example includes a first current source 602 that forces current in the opposite direction as the current sources 502, 504 of FIG. 5 and through the second capacitor 508 of the stimulation path, through the tissue of the body (e.g., $R_{BRAIN}$), and through the first capacitor 506 of the stimulation path. A second current source 604 pulls this current to system ground. While multiple current sources a 602, 604 are shown, it will be appreciated that a single current source may be used instead. Additionally, while current sources are shown in FIG. 6, it will be further appreciated that one or more voltage sources may be used instead.

Figure 7:
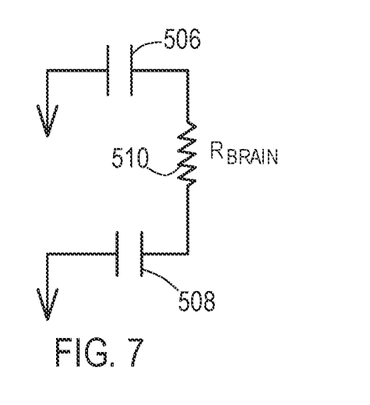
FIG. 7 shows a third stimulation engine circuit configuration used for providing the passive recharge portion of the stimulation waveform.
Figure 8:
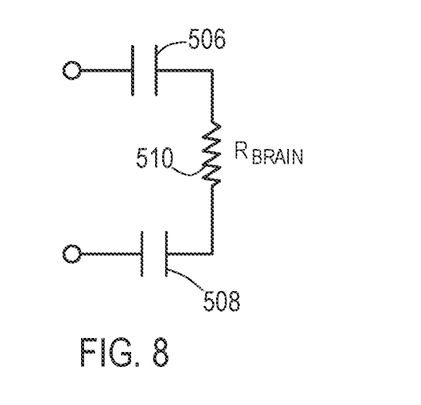
FIG. 8 shows a fourth stimulation engine circuit configuration used for the period of no recharge of the stimulation waveform.

FIG. 7 specifically shows the configuration for providing the period of passive recharge 410. Here the, stimulation engine grounds both stimulation paths to thereby short both capacitors 506, 508 to ground via a low impedance path. As discussed below in relation to FIG. 10, it is this low impedance path that can allow artifacts from non-neurological sources such as an ECG signal of the cardiac system to be captured and amplified. Therefore, this phase is minimized, for instance to a minimal fixed amount such as 264-396 µs, as discussed above in relation to FIG. 4, FIG. 8 specifically shows the configuration for providing the period of no recharge 412. Here, the stimulation engine allows both stimulation paths to electrically float by providing no electrical connection to any particular voltage potential. It is this high impedance path to system ground that results in common mode rejection of the non-neurological signals at the differential amplifier of the sensing circuit.

Figure 9:
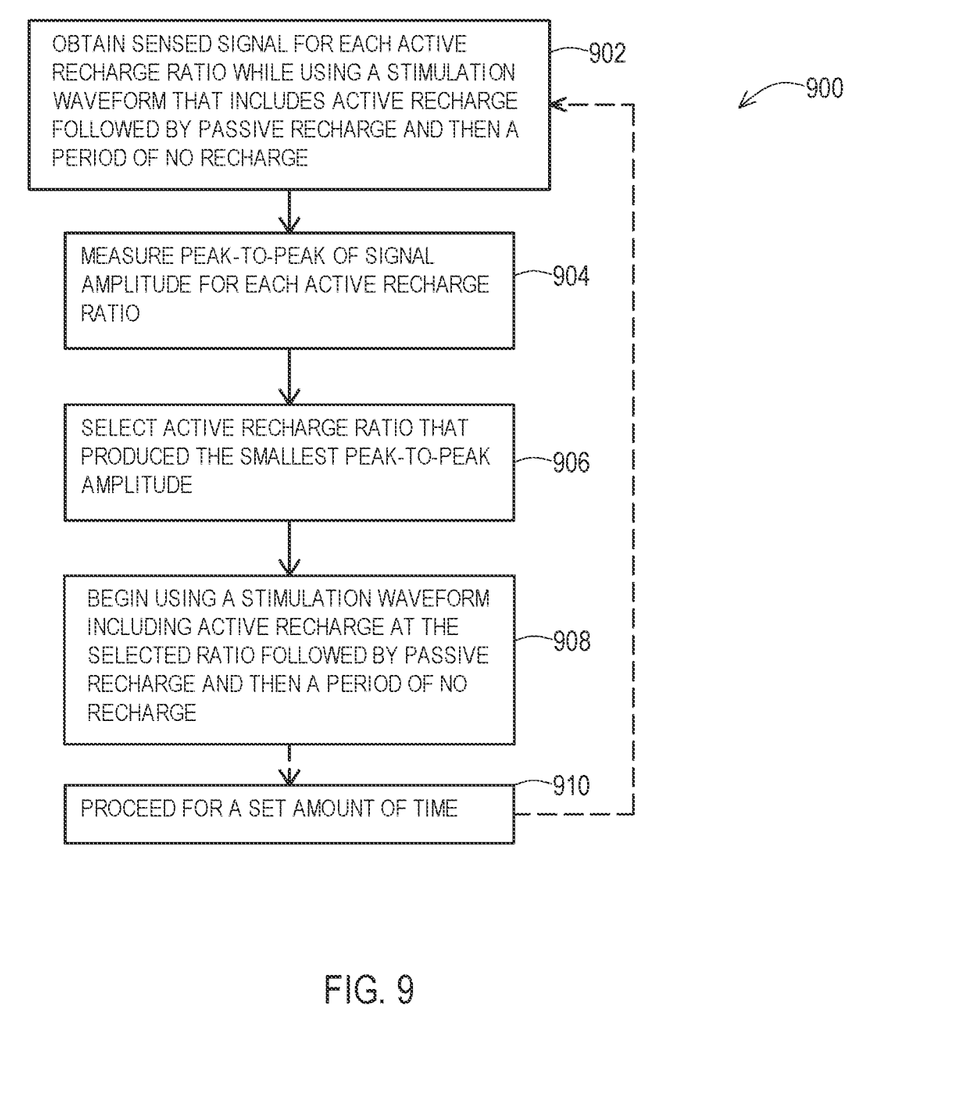
FIG. 9 shows a set of logical operations to determine an appropriate active recharge pulse amplitude ratio relative to the stimulation pulse amplitude in order to minimize non-neurological signals being amplified during sensing.

FIG. 9 shows a set of logical operations that may be used by the controller 202 to set the active recharge ratio that was discussed above. The active recharge ratio of this example sets the amplitude of the active recharge pulse 406 to be some percentage of the amplitude of a baseline active recharge pulse, the baseline typically being the amplitude of the stimulation pulse 402, in order to best clear the capacitors 506, 508 of the stimulation path from the standpoint of minimizing artifacts in the sensed signal. Initially, the stimulation waveform 400 is utilized repeatedly at operation 902, with each iteration using a different active recharge ratio. For example, the first iteration may use a ratio of 0.8, the second may use 0.9, the third may use 1, the fourth may use 1.1, and the fifth may use 1.2.

Once the set of active recharge ratios have each been used, the peak-to-peak amplitude of each resulting sensed signal is measured at an operation 904. The controller 202 then selects the active recharge ratio that produced the smallest peak-to-peak amplitude of the sensed signal at an operation 906. The stimulation engine then begins producing the stimulation waveform 400 using the selected active recharge ratio to set the amplitude of the active recharge pulse 406 at an operation 908. The stimulation engine may then proceed indefinitely, such as until the implantable medical device 102 receives programming that causes the controller 202 to change the stimulation waveform 400 in some manner, which may then trigger the controller 202 to employ the operations of FIG. 9 again to set the active recharge ratio unless the programming has already specified what the active recharge ratio should be.

Another example, indicated by the dashed operational flow of FIG. 9 leading to the operation 910, accounts for the possibility that physiological and device variables may drift over time such that a different active recharge ratio may eventually be the better choice. In this example, the controller 202 may allow the stimulation waveform 400 to continue at the selected active recharge ratio until a set amount of time has been reached from the time the active recharge ratio was initially selected, such as 24 hours. At that point, the controller 202 may repeat the operations 900 of FIG. 9 to again find the active recharge ratio that minimizes the peak-to-peak amplitude and then select that active recharge for use for the next period of time measured at operation 910.

Figure 10:
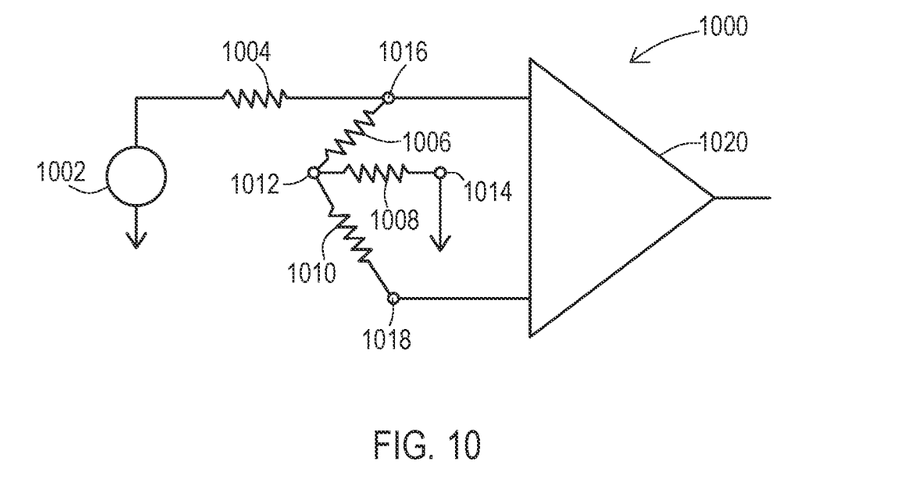
FIG. 10 shows an equivalent circuit of the non-neurological signal source and inputs to a differential amplifier of the sensing circuitry of the medical device when the stimulation engine is providing passive recharge for the stimulation node.

FIG. 10 shows an equivalent circuit 1000 that models a passive recharge configuration. The circuit includes a non-neurological source, such as the heart 1002, and the electrical pathway through the body to nodes 1016, 1018 (e.g., sensing electrodes 118, 120) of the differential amplifier 1020 of the sensing circuit and to a node 1014 (e.g., stimulation node 110) of the stimulation pathway. Resistances 1004, 1006, 1008, and 1010 represent the tissue located between the various nodes. This resistance is typically in the range of 1.5 kilo-ohms. In this passive recharge configuration, the stimulation pathway node 1014 is connected to ground, as in FIG. 7. Thus, there is an electrical pathway that is established where current flows from the heart 1004 and through the tissue resistance 1004 to the sensing node 1016.

Considering the amplifier input of node 1016 does not short to ground, the electrical pathway continues through the tissue resistance 1006 to a central node 1012, which has essentially the same voltage as the sensing node 1018 since there is little to no current through tissue resistance 1010 due to the large input impedance of the amplifier 1020 at node 1018. The electrical pathway continues from central node 1012 through additional tissue resistance 1008 to the stimulation node 1014 which is at system ground. Thus, this flow of current produced by the heart 1002 results in a first voltage on node 1016 while a second voltage occurs on the node 1018. The voltage (VE2) for node 1016 and the voltage (VE0) for node 1018, shown as Eq. 2, are a function of the voltage (VHeart) of the heart 1002 and the resistances of the tissue 1016, 1018 (Rtissue) and the resistance of device leakage 1004 (Rleakage). The voltage (VE2) on node 1016 and the voltage (VE0) on node 1018 are shown below as Eq. 1 and Eq. 2, respectively:

$$VE2 = VHeart*(2*Rtissue)/(Rleakage+(2*Rtissue)) \quad \text{(Eq. 1)}$$

$$VE0 = VHeart*(Rtissue)/(Rleakage+(2*Rtissue)) \quad \text{(Eq. 2)}$$

Figure 12A:
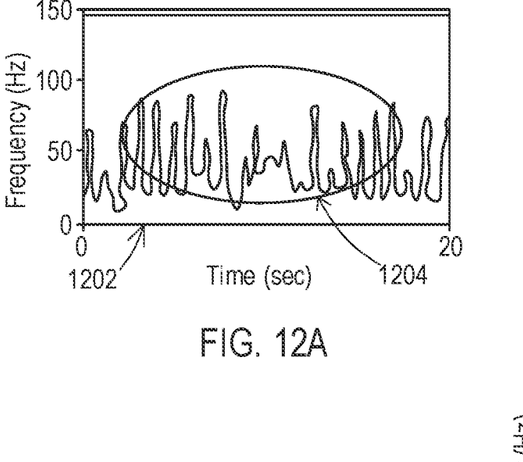
FIG. 12A shows a spectrogram of a sensed neurological signal where the stimulation waveform utilizes only a lengthy passive recharge and significant cardiac energy is present in the sensed signal.
Figure 12B:
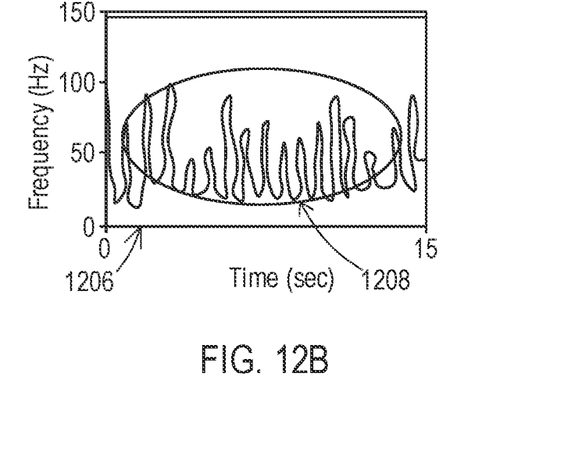
FIG. 12B shows a spectrogram of a sensed neurological signal where the stimulation waveform utilizes a brief active recharge followed by a lengthy passive recharge and significant cardiac energy is present in the sensed signal.
Figure 12C:
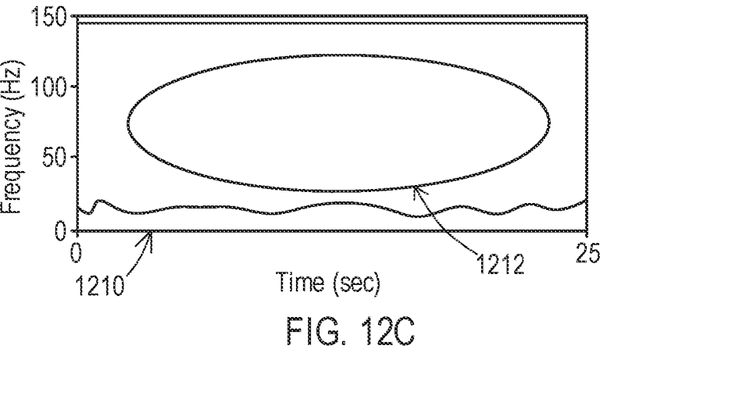
FIG. 12C shows a spectrogram of a sensed neurological signal where the stimulation waveform utilizes a substantial active recharge followed by a brief passive recharge and cardiac energy is present in the sensed signal.

As can be seen from Eq. 1 and Eq. 2, the voltage on node 1018 is half of the voltage on node 1016. Considering the differential amplifier 1020 amplifies the difference between the signal at node 1016 and the signal at 1018, there is a significant amount of the cardiac signal being amplified. FIGS. 12A, 12B, and 12C discussed in more detail below show the results of using this configuration alone, in combination with active recharge but without a period of no recharge, and finally with active recharge, a very brief period of passive recharge, and then a lengthy period of no recharge.

Figure 11:
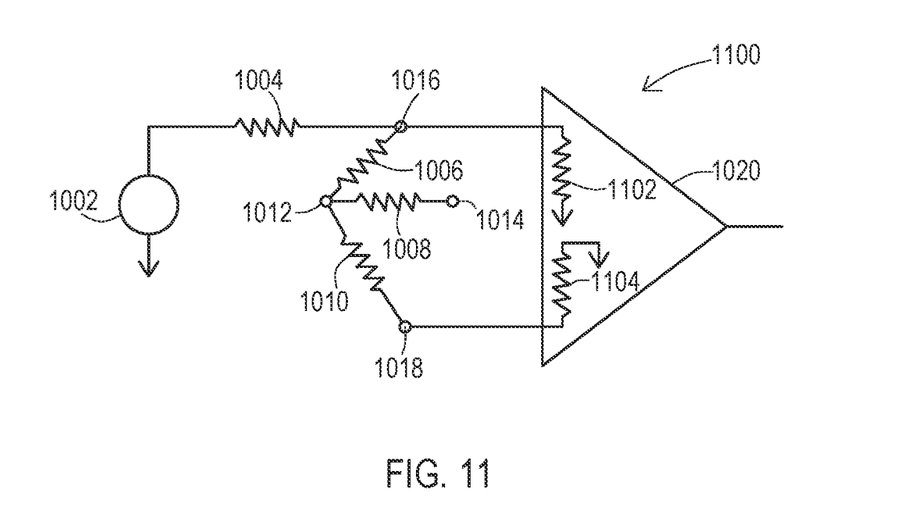
FIG. 11 shows an equivalent circuit of the non-neurological signal source and inputs to a differential amplifier of the sensing circuitry of the medical device when the stimulation engine is providing a period of no recharge to create common mode rejection of the non-neurological signal source.

FIG. 11 shows an equivalent circuit 1100 that models a configuration for the period of no recharge. The circuit includes the non-neurological source, such as the heart 1002, and the electrical pathway through the body to sensing nodes 1016, 1018 and to stimulation node 1014. However, in this no-recharge configuration, the stimulation pathway node 1014 is allowed to electrically float, as in FIG. 8. Thus, there is no longer a low impedance electrical pathway that is established where current can flow from the heart 1004 and through the tissue resistance 1008.

The differential amplifier 1020 has input impedance at the respective differential inputs represented as resistances 1102 and 1104. These are typically in the mega-ohm range, such as 2 mega-ohms. While these input impedances are also present in the passive recharge configuration 1000 of FIG. 10, the low impedance path from node 1014 to ground renders them irrelevant to the voltages at nodes 1016 and 1018. However, in the no-recharge configuration 1100 of FIG. 11, allowing the node 1014 to float results in current only passing into the inputs of the differential amplifier 1020. Therefore, these input impedances are relevant.

Considering these input impedances are drastically larger than those resistances presented by the tissue in the signal path, specifically resistances 1006 and 1010 between nodes 1016 and 1018, the voltage present on node 1016 is essentially the same as the voltage present on node 1018. The voltage on node 1016 is essentially a function of the voltage (VHeart) of the heart 1002, the leakage resistance 1004 (Rleakage), and the amplifier input impedance 1102 (Rinput). The voltage on node 1018 is essentially a function of the voltage (VHeart) of the heart 1002, the leakage resistance 1004 (Rleakage), the amplifier input impedance 1104 (Rinput), and the tissue resistance 1006, 1010 (2*Rtissue). Therefore, the voltage (VE2) on nodes 1016 and the voltage (VE0) on node 1018 are as follows in Eq. 3 and Eq. 4, respectively:

$$VE2 = VHeart*(Rinput)/(Rleakage+Rinput) \quad (Eq.\ 3)$$

$$VE0 = VHeart*(Rinput)/(Rleakage+(2*Rtissue)+Rinput) \quad (Eq.\ 4)$$

One can see that the difference between the sensing electrodes is trivial, with the difference being only the result of adding the double tissue resistance in the denominator. This addition to the denominator, which is an addition of approximately 3 kilo-ohms, is insignificant in comparison with the larger numerator that contains the approximately 2 mega-ohm input resistance. Considering only this trivial difference exists, the cardiac signal is presented primarily as a common mode signal between the two sensing electrodes and therefore common mode rejection of the cardiac signal by the amplifier 1020 occurs.

In the configurations of FIGS. 10 and 11, the physiological signal to be captured, namely the neurological signal emanating from the target site, will present a significant difference from one sensing node 1016 to the other 1018. This physiological signal to be captured propagates from an area near one sensing electrode toward the other, which results in a differential signal between the two sensing electrodes. This differential signal is amplified by the differential amplifier 1020 and ultimately provided to the controller 202 as the sensed signal where the signal may be used for subsequent purposes or stored for later retrieval.

FIGS. 12A-12C show spectrograms of the sensed signal that has been amplified by the differential amplifier 1020. Frequency is represented along the vertical axis while time is presented along the horizontal axis. As illustrated, the trace illustrates the frequencies of most intensity. FIG. 12A shows a spectrogram 1202 demonstrating the result of using only passive recharge. FIG. 12B shows a spectrogram 1206 demonstrating the result of using a brief active recharge with a lengthy passive recharge that extends until time for the next stimulation pulse. As can be seen in both of these spectrograms 1202 and 1206, there is significant cardiac energy spanning significant frequencies (e.g., up to 100 Hz), as illustrated by the vertical spikes. The spikes representing the presence of cardiac energy are apparent in areas indicated by ellipses 1204 and 1208. These intensities of cardiac energy appear in the amplified signal due to the condition shown in FIG. 10.

Transitioning to the spectrogram 1210 of FIG. 12C, according to the stimulation waveform 400 of FIG. 4 where passive recharge is only brief, e.g. 330 µs, there is such a small amount of time of passive recharge that little to no cardiac energy is being captured. Thus, the no-recharge circuit configuration 1100 of FIG. 11 dominates the period of sensing, and because common mode rejection is taking place during the corresponding lengthy period of no recharge, the cardiac energy is eliminated from the sensed signal. The lack of cardiac energy is evident, as there are no longer vertical spikes in the trace in the area indicated by the ellipse 1212.

Utilizing active recharge to more quickly clear the capacitors allows for the lengthy period of no recharge shown in FIG. 12C. However, active recharge requires energy to be provided by the implantable medical device 102. As discussed above and shown in FIG. 6, current sources 602 and 604 force current through the stimulation path capacitors 506, 508 in the reverse direction to more quickly clear the charge that has accumulated during the stimulation pulse. Thus, active recharge may reduce the amount of charge in the battery of the implantable medical device more quickly than if only passive recharge is being used.

Figure 13:
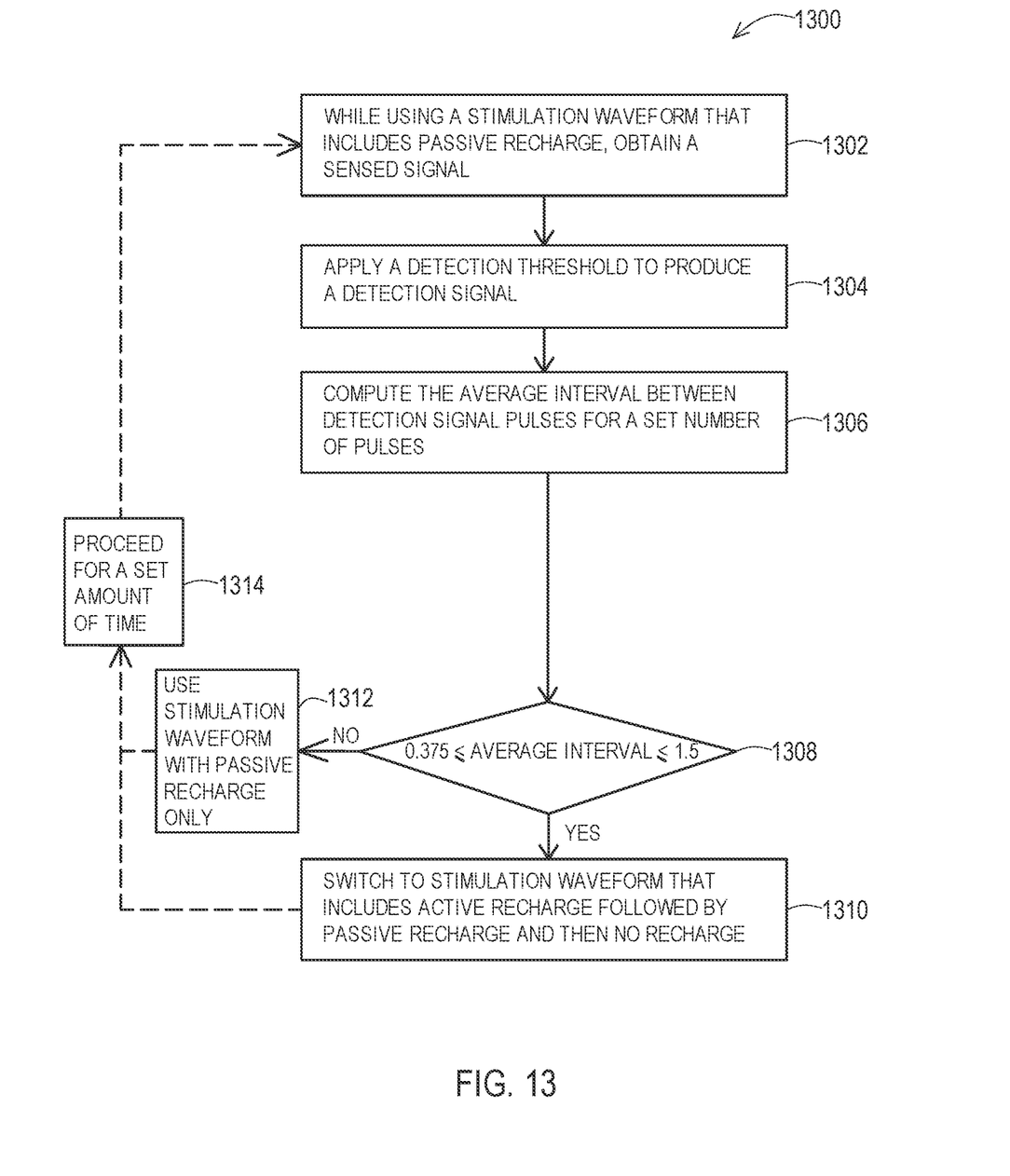
FIG. 13 shows a set of logical operations to determine whether to implement active recharge followed by passive recharge and a period of no recharge.

To account for this increased drain on the battery, some embodiments of the implantable medical device 102 may utilize logical operations like the example 1300 of FIG. 13 to determine whether the active recharge is needed. Due to changes in device condition, patient physiology, and so forth over time, the likelihood of cardiac energy being captured as artifacts in the sensed signal may fluctuate. Therefore, active recharge may be utilized only when necessary to eliminate the unwanted artifacts according to the example 1300.

These logical operations begin by the controller 202 obtaining a sensed signal while using a stimulation waveform that includes lengthy passive recharge at an operation 1302. At this point, this waveform may either be using only passive recharge, such as where active recharge has not yet been required, or may already include both active recharge and passive recharge. However, for implementing this detection process, the period of passive recharge should be significant so that a window for sensing during the passive recharge period allows a significant number of cycles of the non-neurological source. For instance, the passive recharge may be active for 15 seconds to ensure that at least 10 heartbeats have occurred during that period of passive recharge.

Figure 14:
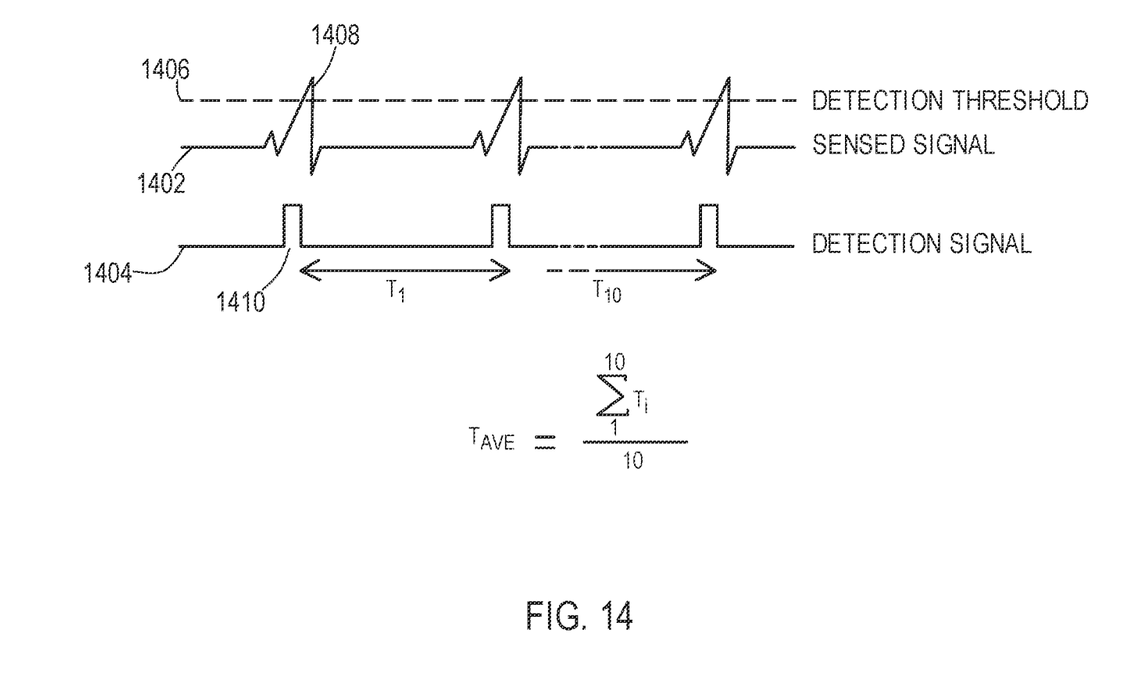
FIG. 14 shows a sensed signal and a detection signal based on the sensed signal and a threshold.

Once the sensed signal has been obtained, the controller 202 applies a detection threshold to produce a detection signal at an operation 1304. FIG. 14 shows an example of the sensed signal 1402 and the detection threshold 1406. The detection threshold is set to some amplitude that is lower than the peak of the non-neurological artifact 1408 present in the sensed signal 1402 but higher than peaks of the neurological signal within the sensed signal 1402. Application of the detection threshold produces the detection signal 1404, which includes a pulse 1410 for each instance of the sensed signal 1402 exceeding the detection threshold 1406.

Upon obtaining the detection signal 1404, the controller 202 computes the average interval ($T_{AVE}$ of FIG. 14) between the detection signal pulses for a set number of pulses, e.g., 10, at an operation 1306. This average interval may then be compared to a range defining a span typical for the non-neurological signal of interest. For instance, a typical pulse rate has anywhere from a 0.375 second interval (i.e., 160 beats per minute) to a 1.5 second interval (i.e., 40 beats per minute). As determined by the controller 202 at a query operation 1308, if the average interval falls outside of the range which indicates that the detection signal is likely not produced by the non-neurological source of interest, then the controller 202 utilizes a mode where only passive recharge is used at an operation 1312. When the average interval does fall within the range, then the controller 202 utilizes the mode that includes active recharge, followed by a brief period of passive recharge, followed by a lengthy period of no-recharge at an operation 1310.

In one embodiment of the example 1300, the logical operations end and the device continues to use the selected mode indefinitely. For instance, the mode may be continued until an external programmer instructs the controller 202 to repeat the operations 1300. In another embodiment, shown with the dashed lines of the operational flow, after the mode is selected at the operation 1310 or 1312, the controller 202 continues with the selected mode for a set period of time, such as 24 hours, at an operation 1314. The controller 202 then repeats the operations beginning at the operation 1302 to again set the mode that is most appropriate at that time. Thus, the implantable medical device 102 operates in a mode that may not be ideal for only as long as the set period of time in operation 1314.

While embodiments have been particularly shown and described, it will be understood by those skilled in the art that various other changes in the form and details may be made therein without departing from the spirit and scope of the invention.

What is claimed is:

1. A method of setting an active recharge ratio of an implantable stimulation device, comprising:
    repeatedly providing from the implantable medical device stimulation waveforms that include a stimulation pulse followed by an active recharge pulse where each stimulation waveform utilizes a different active recharge ratio from other stimulation waveforms being provided where the active recharge ratio is based on an active recharge pulse amplitude relative to a baseline active recharge pulse amplitude;
    sensing at the implantable medical device a sensed signal at a time between each of the stimulation waveforms being provided;
    determining a peak-to-peak amplitude for each sensed signal;
    selecting the active recharge ratio of the stimulation waveform that immediately preceded the sensed signal with the smallest peak-to-peak amplitude; and
    using the selected active recharge ratio in subsequent stimulation waveforms provided by the implantable medical device.

2. The method of claim 1, wherein the baseline active recharge pulse amplitude corresponds to an amplitude of the stimulation pulse.

3. The method of claim 1, wherein the active recharge ratios comprise 0.8, 0.9, 1, 1.1, and 1.2.

4. The method of claim 1, further comprising after using the selected active recharge ratio in subsequent stimulation waveforms, receiving a trigger at the implantable medical device and again repeatedly providing the stimulation waveforms utilizing different active recharge ratios, again sensing at the implantable medical device the sensed signal between the stimulation waveforms, again determining the peak-to-peak amplitude for each sensed signal, again selecting the active recharge ratio that immediately preceded the sensed signal with the smallest peak-to-peak amplitude, and again using the selected active recharge ratio in subsequent stimulation waveforms provided by the implantable medical device.

5. The method of claim 4, wherein the trigger is new stimulation waveform programming.

6. The method of claim 4, wherein the trigger is reaching a set amount of time.

7. The method of claim 1, wherein sensing a sensed signal comprises producing a differential signal while applying common mode rejection.

8. The method of claim 1, wherein the stimulation waveform also includes a period of passive recharge following the active recharge pulse.

9. The method of claim 8, wherein the stimulation waveform also includes a period of no recharge following the passive recharge.

10. An implantable medical device, comprising:
    a stimulation engine that can produce a stimulation waveform including a stimulation pulse and an active recharge pulse;
    a sensing circuit that can obtain a sensed signal;
    a controller that is coupled to the stimulation engine and the sensing circuit, the controller being configured to:
        cause the stimulation engine to repeatedly provide stimulation waveforms that include a stimulation pulse followed by an active recharge pulse where each stimulation waveform utilizes a different active recharge ratio from other stimulation waveforms being provided where the active recharge ratio is based on an active recharge pulse amplitude relative to a baseline active recharge pulse amplitude;
        cause the sensing circuit to sense a sensed signal at a time between each of the stimulation waveforms being provided;
        determine a peak-to-peak amplitude for each sensed signal;
        select the active recharge ratio of the stimulation waveform that immediately preceded the sensed signal with the smallest peak-to-peak amplitude; and
        cause the stimulation engine to use the selected active recharge ratio in subsequent stimulation waveforms.

11. The implantable medical device of claim 10, wherein the baseline active recharge pulse amplitude corresponds to an amplitude of the stimulation pulse.

12. The implantable medical device of claim 10, wherein the active recharge ratios comprise 0.8, 0.9, 1, 1.1, and 1.2.

13. The implantable medical device of claim 10, wherein the controller is further configured to, after using the selected active recharge ratio in subsequent stimulation waveforms, receive a trigger and again cause the stimulation engine to repeatedly provide the stimulation waveforms utilizing different active recharge ratios, again cause the sensing circuit to sense the sensed signal between the stimulation waveforms, again determine the peak-to-peak amplitude for each sensed signal, again select the active recharge ratio that immediately preceded the sensed signal with the smallest peak-to-peak amplitude, and again cause the stimulation engine to use the selected active recharge ratio in subsequent stimulation waveforms.

14. The implantable medical device of claim 13, wherein the trigger is new stimulation waveform programming.

15. The implantable medical device of claim 13, wherein the trigger is reaching a set amount of time.

16. The implantable medical device of claim 10, wherein the sensing circuit senses a sensed signal by producing a differential signal while applying common mode rejection.

17. The implantable medical device of claim 10, wherein the stimulation waveform also includes a period of passive recharge following the active recharge pulse.

18. The implantable medical device of claim 17, wherein the stimulation waveform also includes a period of no recharge following the passive recharge.

* * * * *